(12) United States Patent
Lius et al.

(10) Patent No.: US 11,507,220 B2
(45) Date of Patent: Nov. 22, 2022

(54) ELECTRONIC DEVICE

(71) Applicant: InnoLux Corporation, Miao-Li County (TW)

(72) Inventors: Chandra Lius, Miao-Li County (TW); Kuan-Feng Lee, Miao-Li County (TW)

(73) Assignee: InnoLux Corporation, Miao-Li County (TW)

( * ) Notice: Subject to any disclaimer, the term of this patent is extended or adjusted under 35 U.S.C. 154(b) by 0 days.

(21) Appl. No.: 17/024,646

(22) Filed: Sep. 17, 2020

(65) Prior Publication Data

US 2021/0109636 A1   Apr. 15, 2021

(30) Foreign Application Priority Data

Oct. 10, 2019 (CN) .................... 201910959044.X

(51) Int. Cl.
*G06F 3/041* (2006.01)
*G06V 40/13* (2022.01)

(52) U.S. Cl.
CPC ........ *G06F 3/04164* (2019.05); *G06F 3/0412* (2013.01); *G06V 40/1306* (2022.01)

(58) Field of Classification Search
None
See application file for complete search history.

(56) References Cited

U.S. PATENT DOCUMENTS

| | | | |
|---|---|---|---|
| 2013/0207125 A1 | 8/2013 | Yamazaki | |
| 2015/0254491 A1 | 9/2015 | Mo | |
| 2017/0017340 A1 | 1/2017 | Liu | |
| 2018/0151122 A1 | 5/2018 | Ding | |
| 2018/0173354 A1 | 6/2018 | Abe | |
| 2018/0284926 A1* | 10/2018 | Kim | G06F 3/044 |
| 2018/0348959 A1* | 12/2018 | Lin | G09G 3/3659 |
| 2018/0373393 A1* | 12/2018 | Lerner | G06F 3/0433 |
| 2019/0034688 A1 | 1/2019 | Lee | |
| 2019/0065717 A1 | 2/2019 | Won | |
| 2019/0279590 A1* | 9/2019 | Takahashi | G09G 3/36 |
| 2019/0302951 A1* | 10/2019 | Shepelev | G06F 3/044 |
| 2020/0134285 A1* | 4/2020 | Hung | G06K 9/00013 |
| 2020/0410190 A1* | 12/2020 | Kitchens | G06F 3/0412 |

FOREIGN PATENT DOCUMENTS

| | | |
|---|---|---|
| CN | 107918756 A | 4/2018 |
| CN | 108615504 A | 10/2018 |
| JP | 2015-201164 A | 11/2015 |
| WO | 2019/033355 A1 | 2/2019 |

OTHER PUBLICATIONS

Pranav Koundinya et al., Multi Resolution Touch Panel with Built-in Fingerprint Sensing Support, XP055575836, DATE14, 2014 EDAA, 2014.

* cited by examiner

*Primary Examiner* — Brian M Butcher

(74) *Attorney, Agent, or Firm* — Winston Hsu

(57) ABSTRACT

The present disclosure provides an electronic device including a display unit, a sensor unit, M first signal lines and N second signal lines. The display unit and the sensor unit are electrically connected to N second signal lines through M first signal lines, M and N are natural numbers, and M is greater than N.

5 Claims, 12 Drawing Sheets

ELECTRONIC DEVICE

BACKGROUND OF THE DISCLOSURE

1. Field of the Disclosure

The present disclosure relates to an electronic device; more particularly, an electronic device having a sensor.

2. Description of the Prior Art

In general, fingerprint identification can be applied in identity verification. Therefore, with the continuous advancement of technologies related to electronic devices, sensors having fingerprint identification functions to be integrated into various types of electronic devices and become widely available for users to manage electronic devices directly through fingerprint identification. Additionally, fingerprints can be quickly identified and are difficult to forge; therefore, fingerprint identification technology can provide convenience and security. In recent years, industries have been dedicated to integrating fingerprint identification functions and display functions into the same electronic device while simultaneously providing high resolution display images. Furthermore, sensing technologies are not limited to uses in identifying fingerprints; applications also include image sensing or touch control sensing.

SUMMARY OF THE DISCLOSURE

The present disclosure provides an electronic device including a display unit, a sensor unit, M first signal lines and N second signal lines. The display unit and the sensor unit are electrically connected to N second signal lines through the M first signal lines, M and N are natural numbers and M is greater than N.

These and other objectives of the present disclosure will no doubt become obvious to those of ordinary skill in the art after reading the following detailed description of the embodiment that is illustrated in the various figures and drawings.

DETAILED DESCRIPTION

Figure 1:
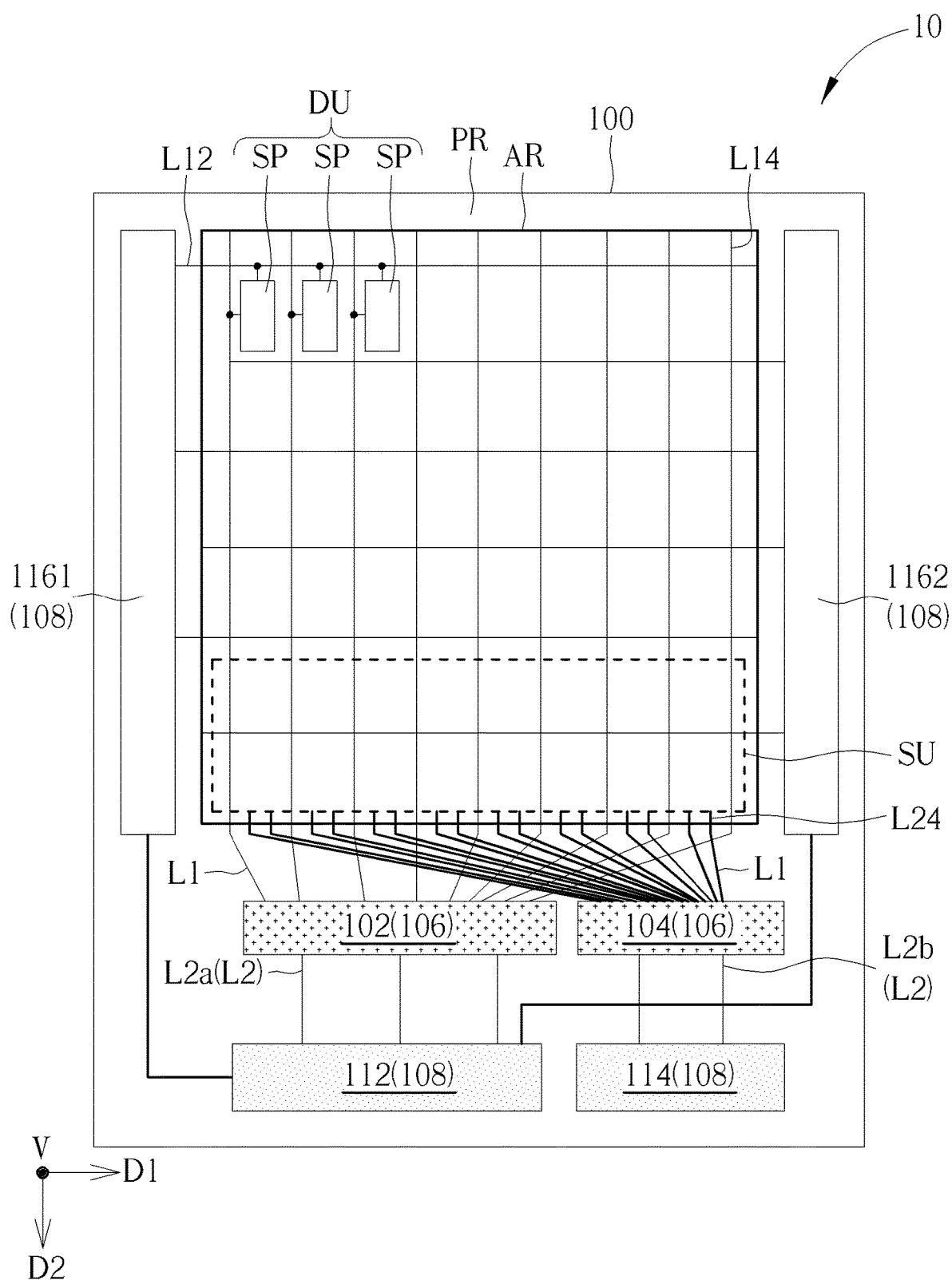
FIG. 1 is a schematic diagram of an electronic device according to a first embodiment of the present disclosure.

The present disclosure may be understood by reference to the following detailed description, taken in conjunction with the embodiments and drawings as described below. It is noted that, for purposes of illustrative clarity and being easily understood by the readers, various drawings of this disclosure may be simplified schematic diagrams that partially illustrate an electronic device; certain components within may not be drawn to scale. In addition, the number and dimension of each component shown in drawings are only illustrative and are not intended to limit the scope of the present disclosure.

Certain terms are used throughout the description and following claims to refer to particular components. As one skilled in the art will understand, electronic equipment manufacturers may refer to a component by different names. This document does not intend to distinguish between components that differ in name but not in function. In the following description and in the claims, the terms "include", "comprise" and "have" are used in an open-ended fashion, and thus should be interpreted to mean "include, but not limited to . . . ".

It will be understood that when an element or layer is referred to as being "on" or "connected to" another element or layer, it can be directly on or directly connected to the other element or layer, or intervening elements or layers may be presented. In contrast, when an element is referred to as being "directly on" or "directly connected to" another element or layer, there are no intervening elements or layers presented.

The term "electrically connected" may indicate a direct connection or an indirect connection. Two elements may be electrically connected by directly contacting each other to transmit electrical signals, and the two elements do not have other elements therebetween. Two electrically connected elements may transmit electrical signals via another element bridging therebetween. Elements that are "electrically connected" may also be considered as elements that are "coupled."

Although terms such as first, second, third, etc., may be used to describe diverse constituent elements, such constituent elements are not limited by the terms. The terms are used only to discriminate a constituent element from other constituent elements in the specification. The claims may not use the same terms, but instead may use the terms first, second, third, etc. with respect to the order in which an element is claimed. Accordingly, in the following description, a first constituent element may be a second constituent element in a claim.

It should be noted that the technical features in different embodiments described in the following description may be replaced, recombined, or mixed with one another to constitute another embodiment without departing from the spirit of the present disclosure.

An electronic device according to the present disclosure may include a display device, an antenna device, or a tiled device, but not limited thereto. The electronic device may be foldable or flexible electronic devices. The electronic device may for example be a display device with touch control functions, image sensing functions, sensing functions for various parameters or fingerprint identification functions. Herein, the display device may be a self-emitting type of organic light-emitting diode (OLED) display, an inorganic light-emitting diode (LED) display, a mini light-emitting diode (mini LED) display, a micro light-emitting diode (micro LED) display, a quantum dot light-emitting diode (quantum dot LED, QLED, QDLED) display, a display using fluorescent materials or phosphorescent materials, other suitable types of displays or a combination of the above types of displays, but not limited thereto. Concepts or principles of the present disclosure may also be applied in non-self-emitting types of displays such as liquid crystal displays (LCDs), but not limited thereto.

The antenna device may for example be a liquid crystal antenna or other types of antenna devices, but the present disclosure is not limited thereto. The tiled device may for example be a tiled display device, a tiled antenna device or a combination thereof, but the present disclosure is not limited thereto. It should be noted that, the electronic device may be a combination of the aforementioned devices, but the present disclosure is not limited thereto. Additionally, an outer shape of the electronic device may be rectangular, spherical, polygonal, a shape with a curved edge or other suitable shapes. The electronic device may have driving systems, control systems, lighting systems, shelving systems etc. as peripheral systems to support the display device, the antenna device or the tiled device. In the following description, the display device is illustrative of an example of the electronic device of the present disclosure but the present disclosure is not limited thereto. When the antenna device or other devices are used as the electronic device, a minimum operating unit thereof may be considered as a sub-pixel of the display device, but not limited thereto.

The sensor of the present disclosure may be applied in optical, thermal, pressure, electromagnetic wave, vibration, sound, gravitational, ultra-sound, length, image, touch or fingerprint sensing without being limited to a particular function. Fingerprint sensing is illustrative of an example of embodiments of the present disclosure, but not limited thereto.

The display device may include a plurality of sub-pixels arranged next to each other in multiple rows. In one embodiment, sub-pixels of a display device may include green, red and blue sub-pixels, or green, red, blue and yellow sub-pixels, or green, red, blue and white sub-pixels, such that colored images may be displayed via various colored light produced by the sub-pixels, but the present disclosure is not limited thereto. Colors produced by the sub-pixels may be designed based on requirements. In another embodiment, the display device may be a single color display device, and all sub-pixels may emit light of a single color, such as white, red or any suitable color. Additionally, a shape of a top view of the sub-pixel may be a rectangle, a parallelogram, a ">" shape or any suitable shape.

Figure 2:
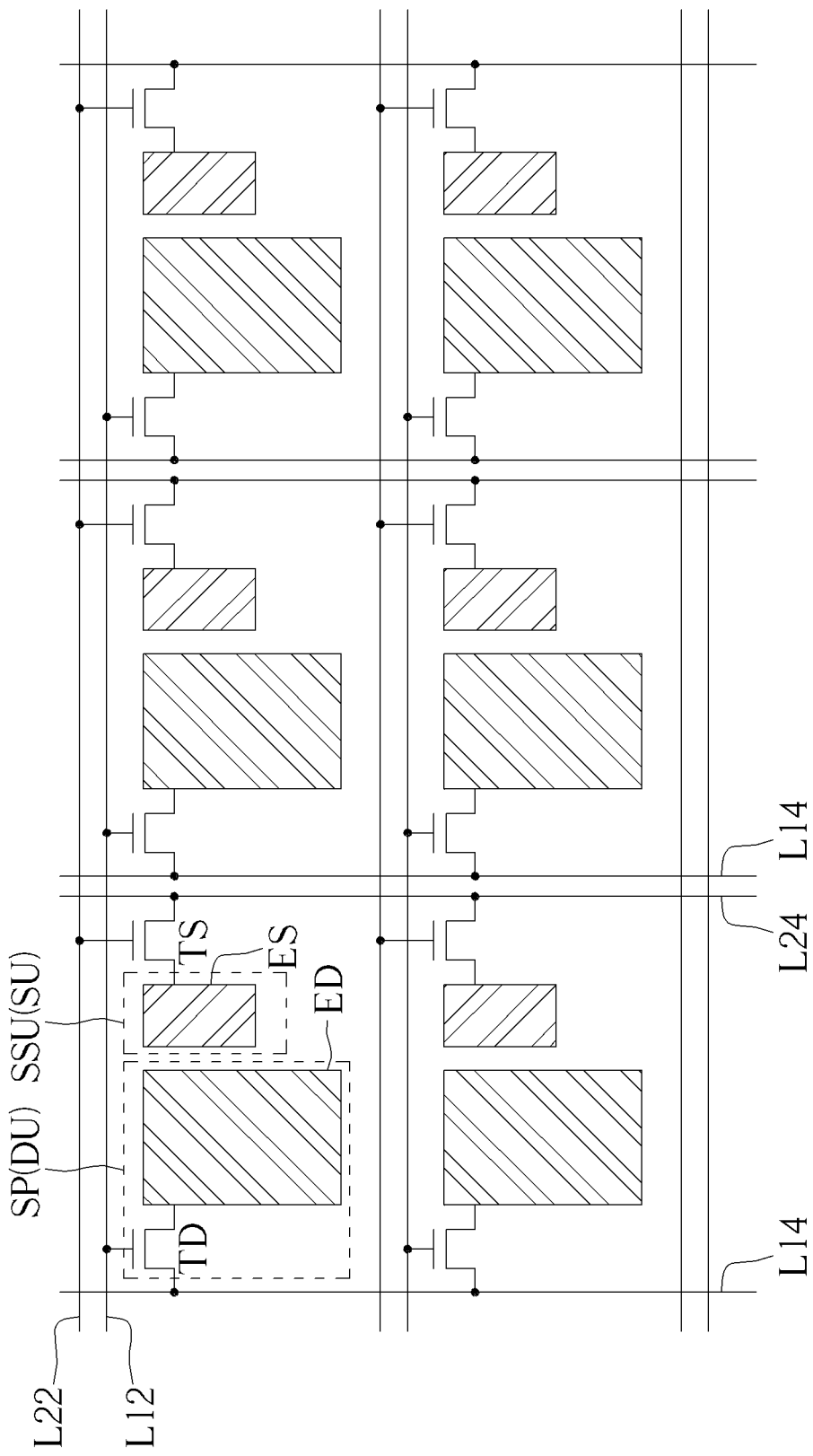
FIG. 2 is a schematic diagram of a sensor unit and a display unit according to the first embodiment of the present disclosure.

Please refer to FIG. 1 and FIG. 2. FIG. 1 is a schematic diagram of an electronic device according to a first embodiment of the present disclosure. FIG. 2 is a schematic diagram of a sensor unit and a display unit according to the first embodiment of the present disclosure. An electronic device 10 of the present embodiment may include a substrate 100 that may include an active region AR and a peripheral region PR adjacent to the active region AR. The peripheral region PR is disposed, for example, on at least one side of the active region AR. As shown in FIG. 1, the peripheral region PR may surround the active region AR. The active region AR may have functions including a display function, a detection function, a sensing function or a light-emitting function, but the present disclosure is not limited thereto. A material of the substrate 100 may include glass, quartz, sapphire, polymer (such as polyimide (PI) or polyethylene terephthalate (PET)) and/or other suitable materials to be used as a flexible substrate or a rigid substrate, but the present disclosure is not limited thereto. Additionally, a shape of a top view of the substrate 100 is not limited to a rectangular shape; the substrate 100 may have any suitable shape.

The electronic device 10 may include a plurality of signal lines, and the signal lines may include a plurality of display scan lines L12 and a plurality of data lines L14 disposed on the substrate 100, but the present disclosure is not limited thereto. In other embodiments, the signal lines may include common lines, emitting control lines, power lines, reset control lines, reference lines, grounding lines, read out lines etc., depending on the type of electronic device. The display scan lines L12 may extend along a first direction D1, the data lines L14 may extend along a second direction D2, and the second direction D2 may not be parallel to the first direction D1. In the present embodiment, the first direction D1 may be orthogonal to the second direction D2, but the present disclosure is not limited thereto. Other signal lines may extend along the first direction D1 or the second direction D2, but the present disclosure is not limited thereto. The display scan lines L12, the data lines L14 or other signal lines may be a straight line, a curved line or a polyline.

In another aspect, the electronic device 10 may include a display unit DU disposed on the substrate 100 and disposed in the active region AR, and the display unit DU may include a plurality of sub-pixels SP. For example, the display unit DU may include three sub-pixels, or the display unit DU may include at least a row of sub-pixels, or the display unit DU may include at least a column of sub-pixels, or the display unit DU may include a plurality of sub-pixels within any given region of the active region AR, or the display unit DU may include all of the sub-pixels within the active region AR, but the present disclosure is not limited thereto. The sub-pixel SP includes an element or structure used for display (such as an electrode of a liquid crystal display unit, an OLED display unit or an inorganic LED display unit) and a switch used to drive the element or structure (such as a thin film transistor).

As shown in FIG. 1, the display scan lines L12 may intersect with the data lines L14 to define multiple regions, wherein one of the sub-pixels SP may be correspondingly disposed within one of the regions, but the present disclosure is not limited thereto. In other embodiments, the regions may also be defined by different intersecting signal lines, or multiple sub-pixels SP may be disposed within one of the regions. Additionally, the display unit DU may be electrically connected to the display scan lines L12 and the data lines L14. For example, every sub-pixel SP may be electrically connected to a corresponding display scan lines L12 and a corresponding data lines L14, but the present disclosure is not limited thereto. In other embodiments, the display unit DU may be electrically connected to different combinations of signal lines depending on driving requirements, and every sub-pixel SP may also be electrically connected to different combinations of corresponding signal lines depending on driving requirements.

The sub-pixel SP may include at least one electrode and at least one thin film transistor. As shown in FIG. 2, the sub-pixel SP may include an electrode ED and a thin film transistor TD, and the electrode ED may be electrically connected to a corresponding thin film transistor TD, but the present disclosure is not limited thereto. In other embodiments, the sub-pixel SP may include multiple electrodes ED or multiple thin film transistors TD. In the present embodiment, the electronic device 10 may for example include a liquid crystal display panel, and the electrode ED may for example be a pixel electrode, but the present disclosure is not limited thereto. In other embodiments, if the electronic device 10 is an OLED display panel or an inorganic LED display panel, the electrode ED may for example be a cathode or an anode. A gate of the thin film transistor TD may be electrically connected to the display scan lines L12, a first end of the thin film transistor TD may be electrically connected to a corresponding data lines L14, and a second end of the thin film transistor TD may be electrically connected to a corresponding electrode ED, but the present disclosure is not limited thereto. Additionally, the first end and the second end of the thin film transistor herein may for example be a source and a drain, or a drain and a source respectively.

As shown in FIG. 1, the electronic device 10 may include a sensor unit SU disposed on the substrate 100 and within a portion of the active region AR, and the sensor unit SU may be integrally disposed with the display unit DU, but the present disclosure is not limited thereto. In other embodiments, the electronic device 10 may also include multiple sensor units SU, the sensor unit SU may also be partially located in the active region AR and partially located in the peripheral region PR, or the sensor unit SU may be entirely located within the peripheral region PR. The sensor unit SU and the display unit DU may also be integrally disposed and partially overlapped, or separately disposed from the display unit DU without overlapping. An area occupied by the sensor unit SU may be greater than, equal to or less than an area occupied by the display unit DU. For example, an area occupied by an electrode ES of the sub-sensor unit SSU may be greater than, equal to or less than an area occupied by an electrode ED of the sub-pixel SP.

As shown in FIG. 2, the signal lines may further include a plurality of sensing scan lines L22 and a plurality of sensing lines L24. The sensing scan lines L22 may extend along the first direction D1, the sensing lines L24 may extend along the second direction D2, and the sensing scan lines L22 and the sensing lines L24 may be electrically connected to a corresponding sensor unit SU, but the present disclosure is not limited thereto. In other embodiments, the sensing scan lines L22 may extend along the second direction D2, and the sensing lines L24 may extend along the first direction D1. Additionally, one of the sensing scan lines L22 may be disposed adjacent to one of the display scan lines L12, and one of the sensing lines L24 may be disposed adjacent to one of the data lines L14. Furthermore, the sensing scan lines L22 and the display scan lines L12 may intersect with the sensing lines L24 and the data lines L14, and the sensing scan lines L22, the display scan lines L12, the sensing lines L24 and the data lines L14 are electrically isolated from each other and may be driven independently, driven in sequence, or driven synchronously. However, configurations of the sensing scan lines L22, the display scan lines L12, the sensing lines L24 and the data lines L14 are not limited thereto.

As shown in FIG. 2, the sensor unit SU may include a plurality of sub-sensor units SSU, one sub-sensor unit SSU may be correspondingly disposed with one sub-pixel SP, and every sub-sensor unit SSU may be electrically connected to a corresponding sensing scan line L22 and a corresponding sensing line L24, but the present disclosure is not limited thereto. In other embodiments, the sub-sensor unit SSU may be electrically connected to different combinations of signal lines depending on driving requirements. The sub-sensor unit SSU may include at least one electrode. As shown in FIG. 2, the sub-sensor unit SSU may include an electrode ES, and the electrode ES may be electrically connected to a corresponding thin film transistor TS, but the present disclosure is not limited thereto. In other embodiments, the sub-sensor unit SSU may include multiple electrodes ES or multiple thin film transistors TS, or the sub-sensor unit SSU may be multiple electrodes ES electrically connected to a corresponding thin film transistor TS, or the sub-sensor unit SSU may be an electrode ES electrically connected to multiple corresponding thin film transistors TS. The gate of the thin film transistor TS may be electrically connected to the sensing scan line L22, a first end of the thin film transistor TS may be electrically connected to a sensing line L24, and a second end of the thin film transistor TS may be electrically connected to the electrode ES, but the present disclosure is not limited thereto.

An optical sensor is illustrative of an example of the sensor unit SU of the present embodiment. Every sub-sensor unit SSU may include an optical sensor (photodiode), for example a PIN-type diode or other suitable photoelectric transducers, and the electrode ES may be a lower electrode electrically connected to an end of the PIN-type diode, but the present disclosure is not limited thereto. The sensor unit SU may also include a capacitive sensor, an ultrasonic sensor, an infrared (IR) sensor or other suitable types of sensors.

As shown in FIG. 1, the electronic device 10 may include a demultiplexer (or demux) 106 disposed on the substrate 100 and in the peripheral region PR. The demux 106 may be formed on the substrate 100 using a thin film deposition process, followed by a photolithography process, followed by an etching process, but the present disclosure is not limited thereto. The demux 106 may include a demux unit 102 (which may also be called a first demux unit) and a demux unit 104 (which may also be called a second demux unit), and the demux unit 102 along with the demux unit 104 may be disposed on a side of the active region AR along the second direction D2, but the present disclosure is not limited thereto. In other embodiments, the demux 106 may only include one of the demux unit 102 and the demux unit 104, or the demux unit 102 and the demux unit 104 may be separately disposed on opposite sides of the active region AR along the second direction D2.

The data lines L14 and the sensing lines L24 may be extended from the active region AR to the peripheral region PR, the data lines L14 may be electrically connected to an output end of a corresponding demux unit 102, and the sensing lines L24 may be electrically connected to an output end of a corresponding demux unit 104, but the present disclosure is not limited thereto. In other embodiments, the data lines L14 may be electrically connected to the output end of the corresponding demux unit 102 and the output end of the corresponding demux unit 104, and the sensing lines L24 may be electrically connected to the output end of the corresponding demux unit 102 and the output end of the corresponding demux unit 104. In other embodiments, the demux 106 may only include one of the demux unit 102 and the demux unit 104. The data lines L14 and the sensing lines L24 may be electrically connected to the same demux unit 102 or the same demux unit 104. Or, only the data lines L14 or only the sensing lines L24 may be electrically connected to the demux unit 102 or the demux unit 104; that is to say, the data lines L14 or the sensing lines L24 may not be electrically connected to the demux unit. In this manner, the demux unit 102 may be electrically connected to the display unit DU, and the demux unit 104 may be electrically connected to the sensor unit SU.

On the other hand, the data lines L14 and the sensing lines L24 may be collectively defined as signal lines L1 (which may also be called first signal lines). Therefore, within the peripheral region PR, M signal lines L1 may include M1 data lines L14 and M2 sensing lines L24. "M" is a number of the quantity of the signal lines L1, "M1" is a number of the quantity of the data lines L14, and "M2" is a number of the quantity of the sensing lines L24. The M1 data lines L14 are electrically connected to the display unit DU, and the M2 sensing lines L24 are electrically connected to the sensor unit SU, wherein M1 may be greater than M2, but the present disclosure is not limited thereto. In other embodiments, M1 may be equal to or less than M2. Alternatively, as shown in FIG. 1, the M1 data lines L14 and the M2 sensing lines L24 within the peripheral region PR may be formed of different conductive layers, and insulating layers are present between conductive layers to prevent electrical short or signal interference between signal lines.

As shown in FIG. 1, the electronic device 10 may include a plurality of signal lines L2 disposed on the substrate 100 and within the peripheral region PR. The signal lines L2 may be connected to an input end of the demux unit 102 or an input end of the demux unit 104. The demux unit 102 may be used to electrically connect the data lines L14 to signal lines L2a (a portion of the signal lines L2), such that signals may be inputted to or outputted from the sub-pixels SP of the display unit DU through a path in a sequence of the signal lines L2a—the demux unit 102—the data lines L14. The demux unit 104 may be used to electrically connect the sensing lines L24 to signal lines L2b (another portion of the signal lines L2), such that signals may be inputted to or outputted from the sub-sensor units SSU of the sensor unit SU through a path in a sequence of the signal lines L2b—the demux unit 104—the sensing lines L24, but the present disclosure is not limited thereto. A quantity of the signal lines L2a may be less than a quantity of the data lines L14, and a quantity of the signal lines L2b may be less than a quantity of the sensing lines L24. Therefore, use of the demux unit 102 and/or the demux unit 104 may reduce a quantity of signal lines used to input signals within the peripheral region PR. In other embodiments, a quantity of the data lines L14 may be greater than, equal to or less than a quantity of the sensing lines L24, and a quantity of the signal lines L2a may be greater than, equal to or less than a quantity of the signal lines L2b.

In summary, the demux 106 may be used to electrically connect M signal lines L1 to N signal lines L2 (which may also be called second signal lines), and "N" is a number of the quantity of the signal lines L2. Or, the display unit DU and the sensor unit SU may be electrically connected to N signal lines L2 via M signal lines L1, wherein M may be greater than N. Values of M, N, M1 and M2 may be positive integers (or natural numbers not including zero). In this manner, a quantity of signal lines within the peripheral region PR may be reduced along with a cost of production, time, or a space occupied by the signal lines within the peripheral region PR.

Additionally, the signal lines L2a and the signal lines L2b may be formed of the same conductive layer or different conductive layers, the signal lines L1 connecting the data lines L14 and the signal lines L1 connecting the sensing lines L24 may be formed of the same conductive layer or different conductive layers, the signal lines L1 and the signal lines L2 may be formed of the same conductive layer or different conductive layers, multiple signal lines L1 may be formed of the same conductive layer or different conductive layers, multiple signal lines L2 may be formed of the same conductive layer or different conductive layers, the data lines L14 and the sensing lines L24 may be formed of the same conductive layer or different conductive layers, multiple data lines L14 may be formed of the same conductive layer or different conductive layers, multiple sensing lines L24 may be formed of the same conductive layer or different conductive layers, and multiple scan lines may be formed of the same conductive layer or different conductive layers.

Figure 3:
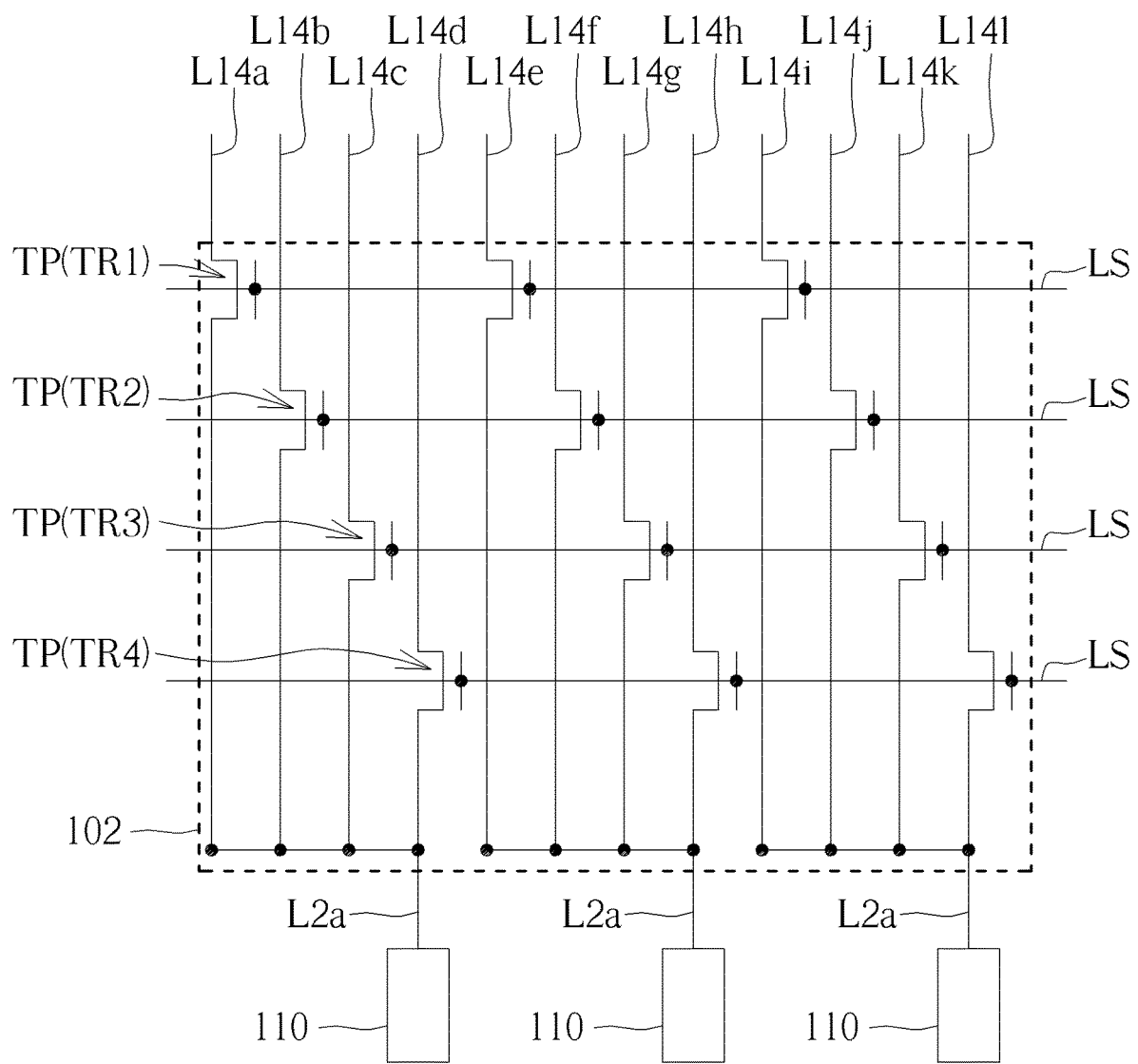
FIG. 3 is a schematic diagram of a demux unit according to the first embodiment of the present disclosure.

Please refer to FIG. 3, which shows a schematic diagram of a demux unit according to the first embodiment of the present disclosure. As an example, the demux unit 102 shown in FIG. 1 is shown in FIG. 3 as including a plurality of thin film transistors TP. The thin film transistors TP may be arranged into four transistor rows, and the gates of the thin film transistors TP of every transistor row may be electrically connected to a switch signal line LS. For example, a data line L14a, a data line L14e, and a data line L14i may be electrically connected to the thin film transistors TP of a transistor row TR1, a data line L14b, a data line L14f, and a data line L14j may be electrically connected to the thin film transistors TP of a transistor row TR2, a data line L14c, a data line L14g, and a data line L14k may be electrically connected to the thin film transistors TP of a transistor row TR3, and a data line L14d, a data line L14h, and a data line L141 may be electrically connected to the thin film transistors TP of a transistor row TR4.

Using the data line L14a, the data line L14b, the data line L14c, and the data line L14d as an illustrative example, these data lines may be electrically connected to a signal line L2a through thin film transistors TP of different transistor rows, and an end of the signal line L2a may be electrically connected to a bonding pad 110 in order to electrically connect to an output end of a driving unit (for example, an integrated circuit chip, IC). Therefore, by activating thin film transistors TP of different transistor rows, signals to be sent by the signal line L2a may be transmitted to the desired data line L14 as thin film transistors turned on or off, thereby achieving an effect of using one input signal line to correspond to multiple output signal lines. However, a quantity of data lines L14 that may be electrically connected to one signal line L2a is not limited to that shown in FIG. 3. The demux unit 104 may also have the same or similar technical features as those mentioned above; for the sake of brevity, a description of such features is omitted herein.

Please refer to FIG. 1, wherein the electronic device 10 may include a driving unit 108 disposed on the substrate 100 and within the peripheral region PR. The driving unit 108 may include an integrated circuit chip 112 and an integrated circuit chip 114, but a quantity of integrated circuit chips is not limited thereto. In other embodiments, the driving unit 108 may only include the integrated circuit chip 112 or only include the integrated circuit chip 114. In other embodiments, the driving unit 108 may include multiple integrated circuit chips 112 or multiple integrated circuit chips 114. The integrated circuit chip 112 may be electrically connected to the signal lines L2a, and the integrated circuit chip 114 may be electrically connected to the signal line L2b. In other words, the driving unit 108 may be electrically connected to the N signal lines L2. For example, the integrated circuit chip 112 of FIG. 1 may be electrically connected to the bonding pads 110 of FIG. 3, and the integrated circuit chip 114 may also have the same or similar technical features as the integrated circuit chip 112. In such manner, the integrated circuit chip 112 (which may also be called a first driving unit) may be electrically connected to the display unit DU through the signal lines L2a, the demux unit 102 and the data lines L14 (or the signal line L1), whereas the integrated circuit chip 114 (which may also be called a second driving unit) may be electrically connected to the sensor unit SU through the signal lines L2b, the demux unit 104 and the sensing lines L24 (or the signal line L1). The signal lines L2 may for example be formed of the same conductive layer, but the present disclosure is not limited thereto. Electrically connecting the sensor unit SU to the independent integrated circuit chip 114 may increase sensing speed and accuracy. In some embodiments, the integrated circuit chip 112 and the integrated circuit chip 114 may be integrated into one integrated circuit chip.

Additionally, the driving unit 108 may further include at least one gate driver circuit. The gate driver circuit may be an integrated circuit chip, or the gate driver circuit may be formed on the substrate 100 using a thin film deposition process, followed by a photolithography process, and followed by an etching process. As shown in FIG. 1, the driving unit 108 may include a gate driver circuit 1161 and a gate driver circuit 1162, and the active region AR may be disposed between the gate driver circuit 1161 and the gate driver circuit 1162 in the second direction D2, but the present disclosure is not limited thereto. In other embodiments, the driving unit 108 may only include the gate driver circuit 1161 or the gate driver circuit 1162, wherein all the scan lines may be driven from a single side. The gate driver circuit 1161 may be electrically connected to a portion of the display scan lines L12, and the gate driver circuit 1162 may be electrically connected to another portion of the display scan lines L12. Additionally, the gate driver circuit 1161 and the gate driver circuit 1162 may be electrically connected to the driving unit 108 (such as the integrated circuit chip 112), but the present disclosure is not limited thereto.

In other embodiments, the gate driver circuit 1161, the gate driver circuit 1162, the integrated circuit chip 112 or multiple integrated circuit chips 114 may be separately, or at least partially integrated/collected, and then electrically connected to an external control circuit board. In other embodiments, the gate driver circuit 1161, the gate driver circuit 1162, the integrated circuit chip 112 or multiple integrated circuit chips 114 may be located outside of the substrate 100 instead of being disposed on the substrate 100, while using a circuit board to be electrically connected to the bonding pad 110 and provide driving signals.

In some embodiments, the driving unit 108 (such as the integrated circuit chip 112, the integrated circuit chip 114, the gate driver circuit 1161 or the gate driver circuit 1162) may be disposed on the substrate 100 via a chip bonding process. In some embodiments, the driving unit 108 may be electrically connected to the bonding pads of the substrate 100 through a flexible printed circuit (FPC). In some embodiments, the driving unit 108 may be formed on a flexible film (for example, formed as a chip on film, COF) and electrically connected to the bonding pads on the substrate 100.

It is worth noting that, an abovementioned concept of reducing a quantity of signal lines electrically connected to the display unit DU or the sensor unit SU using the demux unit 106 in the peripheral region PR may be applied in the remaining embodiments of the present disclosure. The quantity of the display scan lines electrically connected to the gate driver circuit 1161 or the gate driver circuit 1162 may also be reduced through a demux unit.

The electronic device of the present disclosure is not limited to the abovementioned embodiments; other embodiments will be disclosed in the description below. However, for simplicity and to emphasize differences between each embodiment and the aforementioned embodiments, identical reference signs will be used for identical components and will not be described repeatedly.

Figure 4:
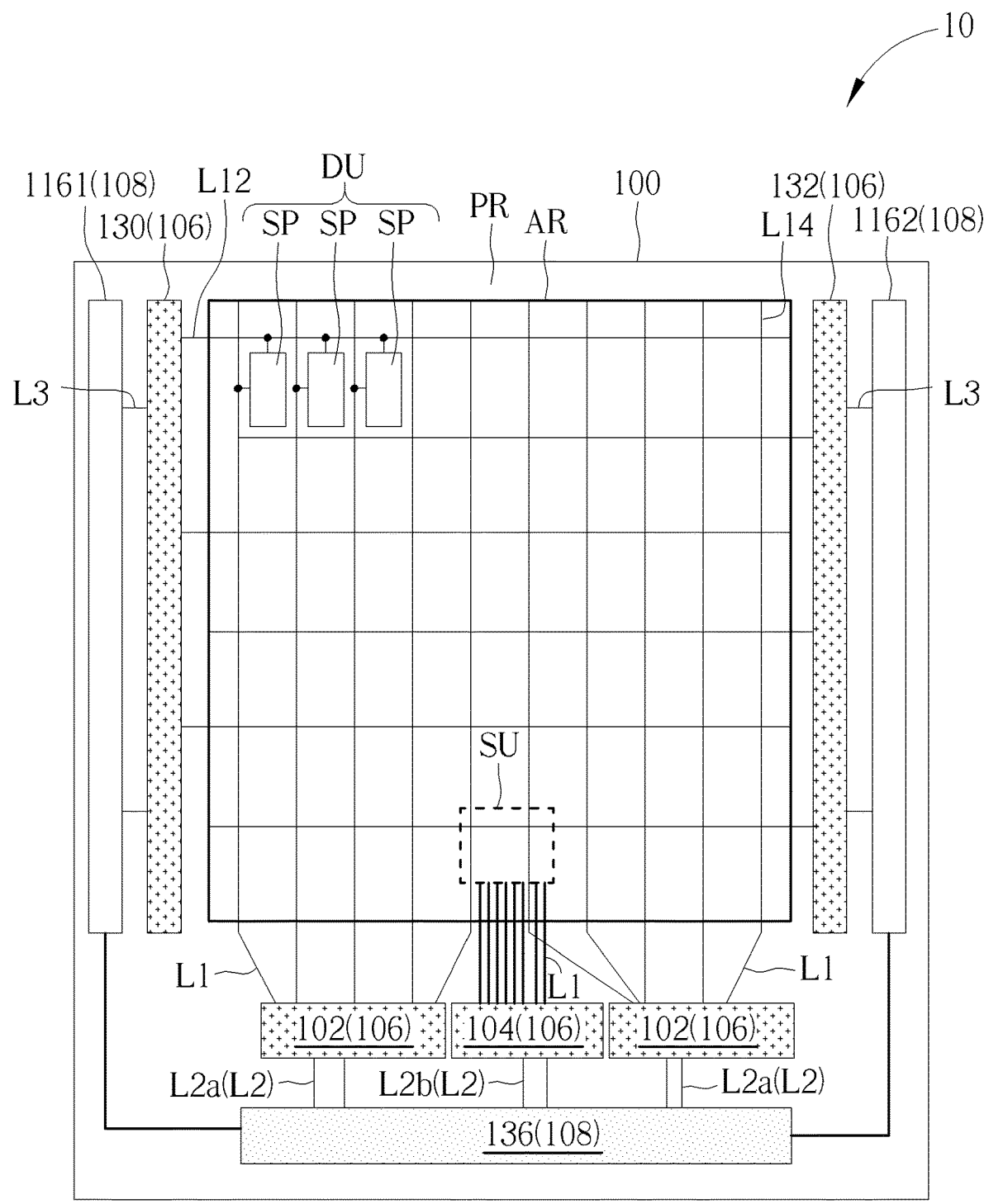
FIG. 4 is a schematic diagram of an electronic device according to a second embodiment of the present disclosure.
Figure 5:
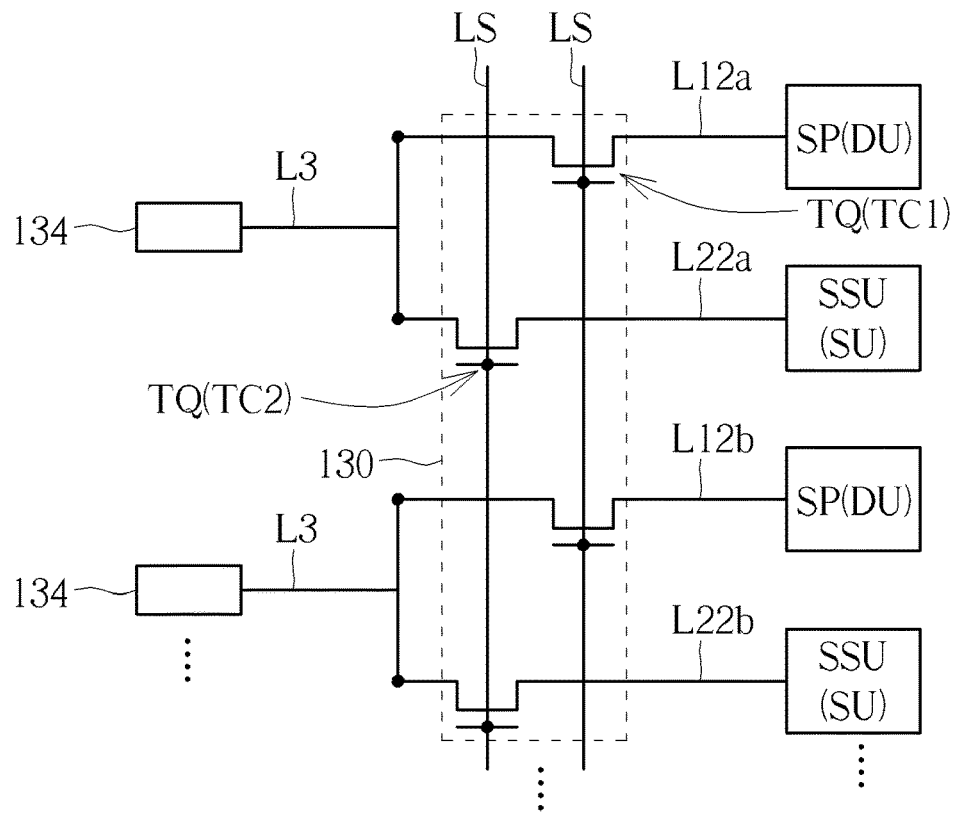
FIG. 5 is a schematic diagram of a demux unit according to the second embodiment of the present disclosure.

Please refer to FIG. 4 and FIG. 5, FIG. 4 is a schematic diagram of an electronic device according to a second embodiment of the present disclosure, and FIG. 5 is a schematic diagram of a demux unit according to the second embodiment of the present disclosure. A difference between the present embodiment and the first embodiment is that the demux 106 of the present embodiment (as shown in FIG. 4) may further include a demux unit 130 and a demux unit 132. The demux unit 130 and the demux unit 132 may be disposed on opposite sides of the active region AR in the first direction D1. For example, the demux unit 130 may be disposed between the gate driver circuit 1161 and the active region AR, and the demux unit 132 may be disposed between the gate driver circuit 1162 and the active region AR, but the present disclosure is not limited thereto.

As shown in FIG. 5, wherein a portion of the demux unit 130 is shown as an illustrative example, the demux unit 130 may include a plurality of thin film transistors TQ that are arranged, for example, as two transistor columns, and the gates of the thin film transistors TQ of each transistor column may be electrically connected to a switch signal line LS. For example, a display scan line L12a and a display scan line L12b may be electrically connected to the thin film transistors TQ of a transistor column TC1; a sensing scan line L22a and a sensing scan line L22b may be electrically connected to the thin film transistors TQ of a transistor column TC2. The display scan line L12a and the sensing scan line L22a may be electrically connected to a signal line L3 through thin film transistors TQ in different transistor columns; the display scan line L12b and the sensing scan line L22b may also be electrically connected to another signal line L3 through thin film transistors TQ of different transistor columns. In FIG. 5, the display scan lines L12 and the sensing scan lines L22 may be alternately disposed; the thin film transistors TQ electrically connected to the display scan lines L12 and the thin film transistors TQ electrically connected to the sensing scan lines L22 may also be alternately disposed, but the present disclosure is not limited thereto. In such manner, a condition in which the display scan line L12b and the sensing scan line L22b crossing over each other in the peripheral region PR may be avoided. Additionally, an end of every signal line L3 may be electrically connected to a bonding pad 134, and the bonding pad 134 may be electrically connected to the gate driver circuit 1161 of FIG. 4. In other embodiments, in which the gate driver circuit 1161 is not an integrated circuit chip, the bonding pad 134 is not required.

In other words, within the peripheral region PR, an M signal lines may include an M3 display scan lines L12 and an M4 sensing scan lines L22, "M" is a number of the quantity of the signal lines, "M3" is a number of the quantity of the display scan lines L12, and "M4" is a number of the quantity of the sensing scan lines L22. The M3 display scan lines L12 are electrically connected to the display unit DU, and the M4 sensing scan lines L22 are electrically connected to the sensor unit SU; here, M3 may be greater than M4, but the present disclosure is not limited thereto. In other embodiments, M3 may be equal to or less than M4. Additionally, the demux unit 130 may be used to electrically connect the abovementioned M signal lines (such as the display scan lines L12 or the sensing scan lines L22) to the N signal lines (such as the signal lines L3), or the display unit DU and the sensor unit SU may both be electrically connected to the N signal lines through the M signal lines, wherein "N" is a number of the quantity of the signal lines, and M is greater than N. The numbers M3 and M4 may be positive integers (or natural numbers not including zero). In this manner, a quantity of signal lines within the peripheral region PR may be reduced along with the cost of production, time, or the space occupied by the signal lines within the peripheral region PR.

When the sub-sensor unit SSU is to be driven, the thin film transistor TQ of the transistor column TC2 may be turned on through one of the switch signal lines LS, and when the sub-pixel SP is to be driven, the thin film transistor TQ of the transistor column TC1 may be turned on through another one of the switch signal lines LS. By turning on the thin film transistors TQ of different transistor columns, signal lines L3 may transmit signals to the desired display scan lines L12 or the sensing scan lines L22. However, the quantity of display scan lines L12 or the quantity of sensing scan lines L22 that maybe electrically connected to one signal line L3 is not limited to what is shown in FIG. 5. The demux unit 132 may also have technical features identical or similar to those mentioned above; for the sake of brevity, such features will not be described.

On the other hand, the present embodiment is different from the first embodiment in that an area of the sensor unit SU of the present embodiment (shown in FIG. 4) may be smaller than an area of the sensor unit SU of the first embodiment, but the present disclosure is not limited thereto. Additionally, the demux 106 of the present embodiment may include two demux units 102 and one demux unit 104, and the demux unit 104 may be disposed between two demux units 102, but the present disclosure is not limited thereto. Wherein, one of the demux units 102 may be electrically connected to a portion of the data lines L14, and the other demux unit 102 may be electrically connected to another portion of the data lines L14. Additionally, the demux units 102 and the demux unit 104 may be electrically connected to the same integrated circuit chip 136 of the driving unit 108 through the signal lines L2, and the integrated circuit chip 136 may be electrically connected to the gate driver circuit 1161 and the gate driver circuit 1162, but the present disclosure is not limited thereto.

Figure 6:
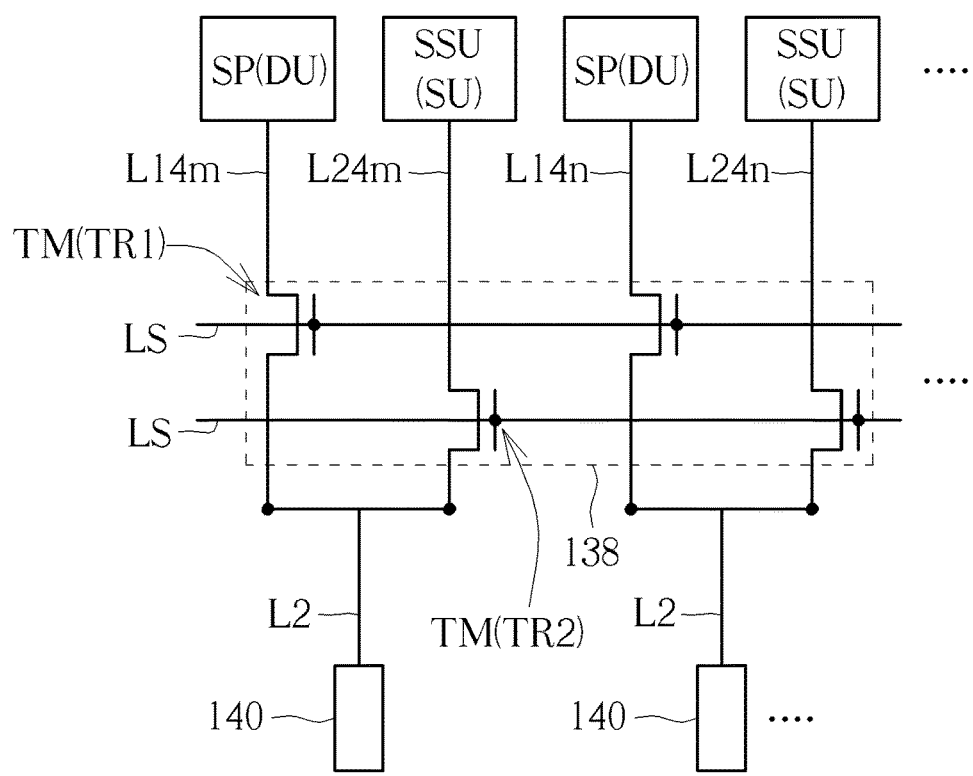
FIG. 6 is a schematic diagram of a demux unit according to a third embodiment of the present disclosure.

Furthermore, please refer to FIG. 6, which is a schematic diagram of a demux unit according to a third embodiment of the present disclosure. The present embodiment differs from the second embodiment in that, in the present embodiment, the demux units 102 electrically connecting the data lines L14 and the demux unit 104 electrically connecting the sensing lines L24 in FIG. 4 may be integrated into one demux unit 138. For example, the demux unit 138 may include a plurality of thin film transistors TM arranged into two transistor rows, and the gates of the thin film transistors TM of every transistor row may be electrically connected to one switch signal line LS. For example, a data line L14$m$ and a data line L14$n$ may be electrically connected to the thin film transistors TM of the transistor row TR1, and a sensing line L24$m$ and a sensing line L24$n$ may be electrically connected to the thin film transistors TM of a transistor row TR2. The data line L14$m$ and the sensing line L24$m$ may be electrically connected to a signal line L2 through the thin film transistors TM of different transistor rows, and the data line L14$n$ and the sensing line L24$n$ may also be electrically connected to another signal line L2 through the thin film transistors TM of different transistor rows. In FIG. 6, the data lines L14 and the sensing lines L24 may be alternately disposed; the thin film transistors TM electrically connected to the data lines L14 and the thin film transistors TM electrically connected to the sensing lines L24 may also be alternately disposed, but the present disclosure is not limited thereto. In such manner, a condition in which the data lines L14 and the sensing lines L24 crossing over each other in the peripheral region PR may be avoided. Additionally, an end of every signal line L2 may be electrically connected to a bonding pad 140, and the bonding pad 140 may be electrically connected to an integrated circuit chip. In other embodiments, the bonding pads 140 may not be required.

Figure 7:
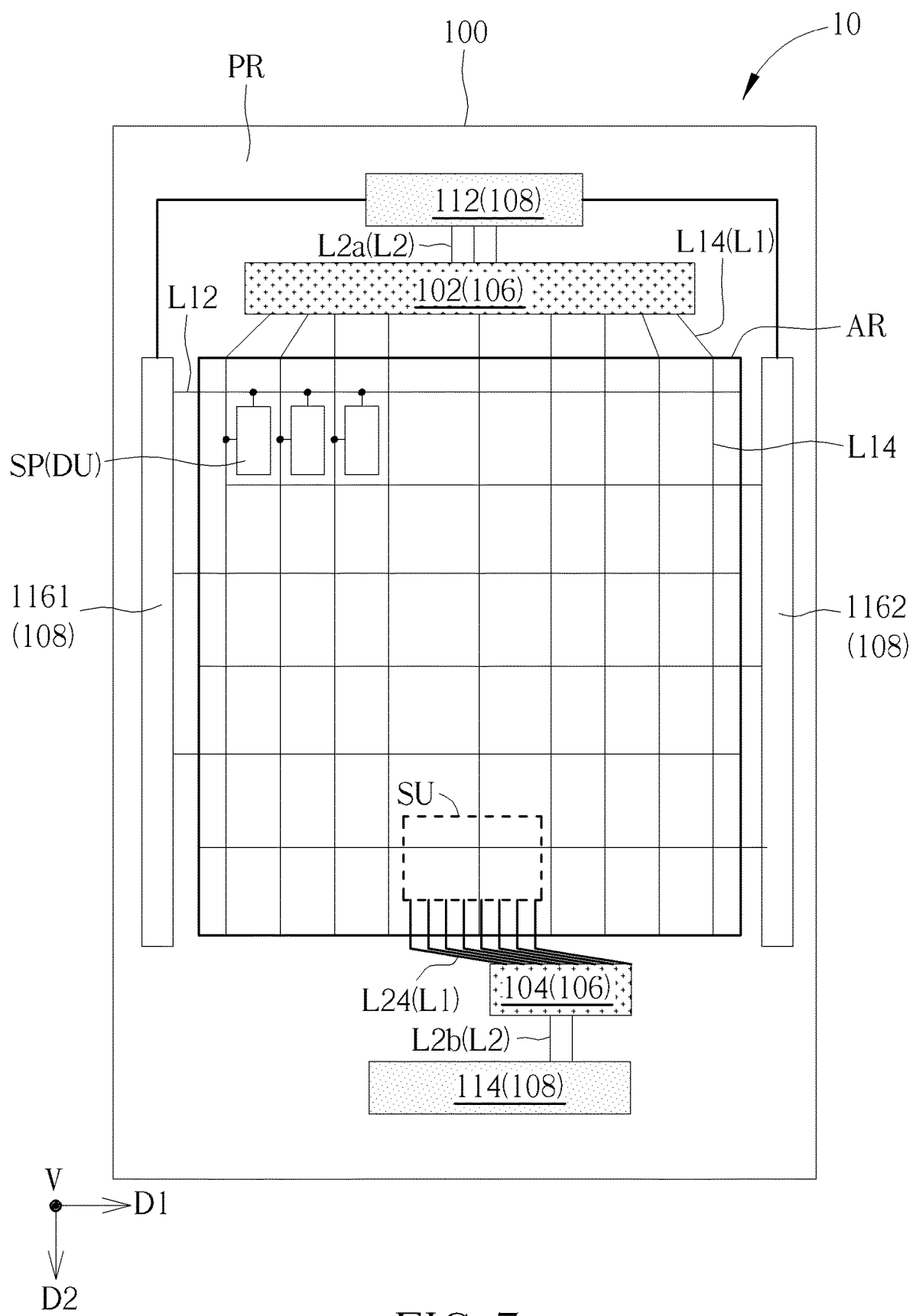
FIG. 7 is a schematic diagram of an electronic device according to a fourth embodiment of the present disclosure.

Please refer to FIG. 7, which is a schematic diagram of an electronic device according to a fourth embodiment of the present disclosure. A difference between the present embodiment and the first embodiment is that the demux unit 102 and the demux unit 104 of the present embodiment may be disposed on opposite sides of the active region AR in the second direction D2; the integrated circuit chip 112 and the integrated circuit chip 114 may also be disposed on opposite sides of the active region AR in the second direction D2, but the present disclosure is not limited thereto. In such manner, a condition in which the data lines L14 and the sensing lines L24 crossing over each other in the peripheral region PR may be avoided. On the other hand, an area of the sensor unit SU of the present embodiment may be smaller than an area of the sensor unit SU of the first embodiment, but the present disclosure is not limited thereto.

Figure 8:
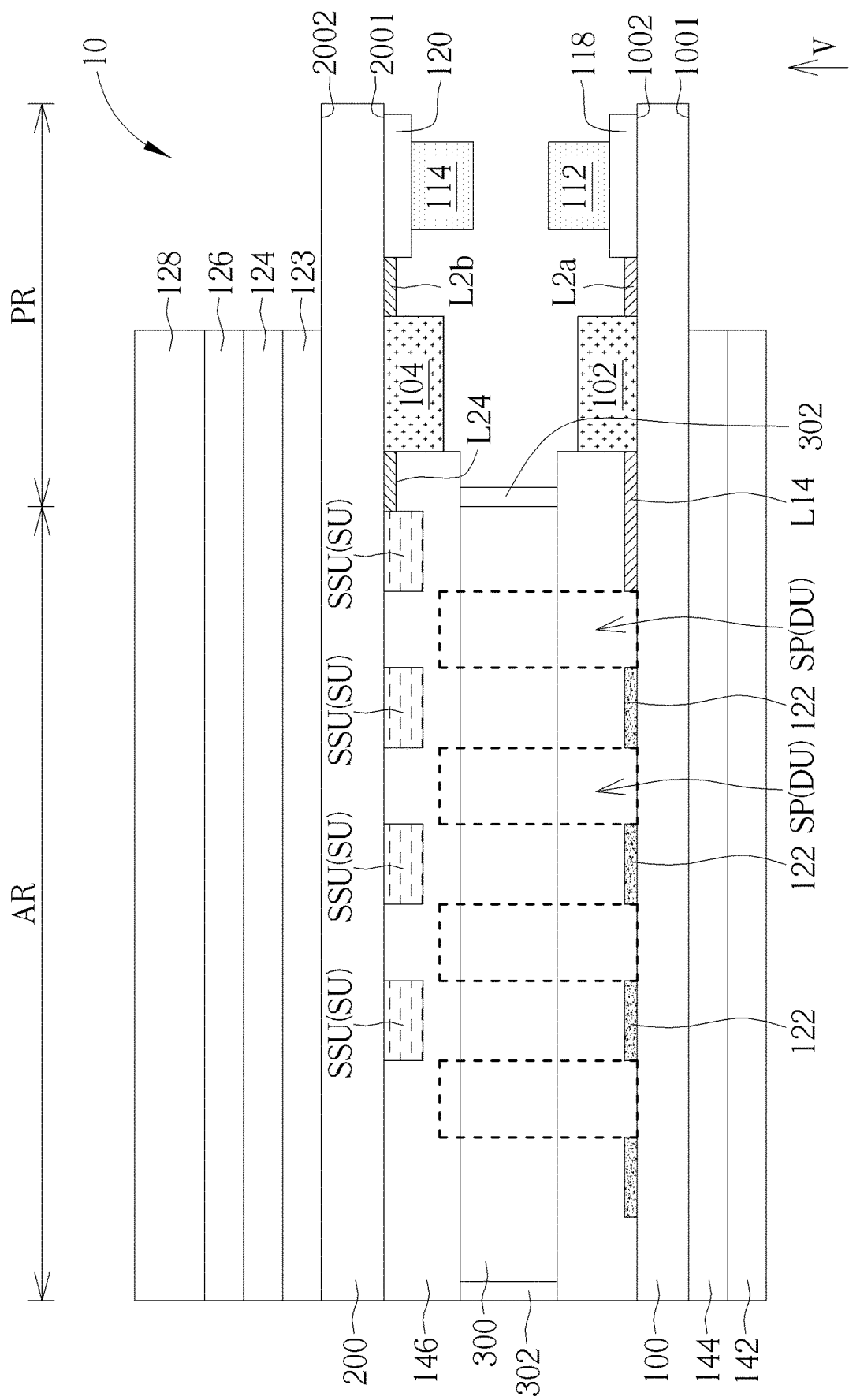
FIG. 8 is a schematic sectional view of an electronic device according to a fifth embodiment of the present disclosure.

Please refer to FIG. 8, which is a schematic sectional view of an electronic device according to a fifth embodiment of the present disclosure. The electronic device 10 may include a substrate 100, a substrate 200 and a liquid crystal layer 300. The substrate 100 and the substrate 200 may be disposed opposite each other, and the liquid crystal layer 300 may be disposed between the substrate 100 and the substrate 200. Additionally, a sealant 302 may be disposed between the substrate 100 and the substrate 200 and on a perimeter of the liquid crystal layer 300. The display unit DU (such as the sub-pixels SP), the demux unit 102 and the integrated circuit chip 112 maybe disposed on the substrate 100, and the sensor unit SU (such as the sub-sensor units SSU), the demux unit 104 and the integrated circuit chip 114 may be disposed on the substrate 200, but the present disclosure is not limited thereto. In other embodiments, the display unit DU, the demux unit 102 or the integrated circuit chip 112 may also be disposed on the substrate 200; on the other hand, the sensor unit SU, the demux unit 104 or the integrated circuit chip 114 may also be disposed on the substrate 100. In other embodiments, the demux unit 102, the demux unit 104, the sealant 302 or the liquid crystal layer 300 may also be overlapped along a normal direction of the substrate 100.

The substrate 200 may have a surface 2001 and a surface 2002 that are opposite to each other, and the sensor unit SU, the demux unit 104 and the integrated circuit chip 114 of the present embodiment may be disposed on the surface 2001, but the present disclosure is not limited thereto. Additionally, the electronic device 10 may include a spectral modulation structure 146 disposed on the surface 2001. The spectral modulation structure 146 may include a color filter or quantum dot layers to modulate a spectrum of light passing through, in order to achieve an effect of color or brightness adjustment. The spectral modulation structure 146 may also include a black matrix to separate different regions of the spectral modulation structure 146 so as to differentiate the display units, but the present disclosure is not limited thereto. The electronic device 10 may further include a backlight module (not shown) disposed adjacent to the substrate 100 and emitting in a V direction; a greyscale of the brightness of the electronic device 10 may be adjusted through a liquid crystal display unit DU with a polarizer.

Within the peripheral region PR, the data lines L14 on the substrate 100 may extend to the demux unit 102, an end of one of the data lines L14 may be electrically connected to the demux unit 102, and another end of one of the data lines L14 may be electrically connected to the display unit DU (or the sub-pixel SP) inside the active region AR. The demux unit 102 may electrically connect to the integrated circuit chip 112 through the signal lines L2a. For example, an end of one of the signal lines L2a may electrically connect to a bonding pad, and the bonding pad may electrically connect to a bonding pad on the integrated circuit chip 112 through a conductive element 118. The conductive element 118 may, for example, include an anisotropic conductive film (ACF), but the present disclosure is not limited thereto.

On the other hand, the sensing lines L24 on the surface 2001 of the substrate 200 may extend to the demux unit 104. An end of one of the sensing lines L24 may be electrically connected to the demux unit 104, and another end of one of the sensing lines L24 may be electrically connected to the sensor unit SU (or the sub-sensor unit SSU) inside the active region AR. The demux unit 104 may electrically connect to the integrated circuit chip 114 through the signal lines L2b. For example, an end of one of the signal lines L2b may be electrically connected to a bonding pad, and the bonding pad may be electrically connected to a bonding pad of the integrated circuit chip 114 through a conductive element 120. The conductive element 120 may for example include an anisotropic conductive film (ACF), but the present disclosure is not limited thereto. In some embodiments, the integrated circuit chip 114 may be omitted; or the integrated circuit chip 114 may be disposed on a surface 1002 of the substrate 100; or the demux unit 104 may be electrically connected to the integrated circuit chip 112 disposed on the substrate 100 or other integrated circuit chips.

Within the active region AR, a non-transparent element 122 may be disposed on the substrate 100 and located on a side of each sub-pixel SP; or, the non-transparent element 122 may be disposed between adjacent sub-pixels SP, but the present disclosure is not limited thereto. The non-transparent element 122 may, for example, include the display scan lines L12, the data lines L14, the thin film transistors, or other non-transparent elements or non-transparent layers, but the present disclosure is not limited thereto. When the sensor unit SU is an optical sensor unit, a semiconductor material of a PIN-type diode utilized in the sub-sensor unit SSU may be non-transparent. Therefore, along the V direction, the sub-sensor unit SSU may be disposed on the non-transparent element 122 and not overlap with the sub-pixel SP at an aperture that allows light to pass through, such that light from the backlight module may pass through the sub-pixel SP without being blocked by the sub-sensor unit SSU. By hiding the non-transparent element 122 under the sub-sensor unit SSU, an aperture ratio of the sub-pixel SP and an amount of light passing through may be increased. The direction V may, for example, be a direction perpendicular to a surface of the substrate 100, but the present disclosure is not limited thereto. In some embodiments, the sub-sensor unit SSU may also overlap with the thin film transistor TD of the sub-pixel SP, but not overlap with the electrode ED (such as a pixel electrode) of the sub-pixel SP. Additionally, the thin film transistors TD (not shown in FIG. 8) of the sub-pixels SP may be disposed between the liquid crystal layer 300 and the substrate 100 or between the liquid crystal layer 300 and the substrate 200; the electrodes ED (such as a pixel electrode, not shown in FIG. 8) of the sub-pixels SP may be disposed between the liquid crystal layer 300 and the substrate 100 or between the liquid crystal layer 300 and the substrate 200, but the present disclosure is not limited thereto.

In some embodiments, if the semiconductor material of the PIN-type diode is transparent, the sub-sensor unit SSU may overlap with the sub-pixel SP. In some other embodiments, the sensor unit SU may be a capacitive sensor unit. In such scenarios, since the electrode of the sub-sensor unit SSU may be transparent (with high transmittance) and have minimal effect on the light passing through the sub-pixel SP, the sub-sensor unit SSU may overlap, partially overlap, or not overlap at all with the sub-pixel SP. The sensor unit SU may also include an ultrasonic sensor, an infrared (IR) sensor or other suitable types of sensors. When the sensor unit SU includes IR sensors, the sub-sensor unit SSU may be configured at a position away from metal layers of the electronic device 10, in order to prevent IR sensors being affected by the metal layers.

As shown in FIG. 8, the electronic device 10 may further include an adhesive layer 123, a polarizer 124, an adhesive layer 126 and a cover 128. The adhesive layer 123 may be disposed on the surface 2002 of the substrate 200, the polarizer 124 may be disposed on the adhesive layer 123, the cover 128 may be disposed on an outermost side of the electronic device 10, and the adhesive layer 126 may be disposed between the cover 128 and the polarizer 124, but the present disclosure is not limited thereto. On the other hand, the substrate 100 may also have a surface 1001 and a surface 1002 that are opposite each other. The display unit DU, the demux unit 102 and the integrated circuit chip 112 of the present embodiment may be disposed on the surface 1002. Additionally, the electronic device 10 may further include a polarizer 142 and an adhesive layer 144. The polarizer 142 and the adhesive layer 144 may be disposed on the surface 1001 of the substrate 100, and the adhesive layer 144 may be disposed between the polarizer 142 and the substrate 100. For example, the polarizer 124 and the polarizer 142 may include linear polarizers, circular polarizers, polarizers with phase retardation layers, polarizers with anti-reflection layers or polarizers with explosion-proof layers, and the cover 128 may include a cover glass, but the present disclosure is not limited thereto.

It is worth noting that, the abovementioned concept of reducing a quantity of signal lines electrically connected to the display unit DU or the sensor unit SU by the demux 106 (such as the demux unit 102 or the demux unit 104) in the peripheral region PR of the first embodiment may also be applied in the present embodiment.

Figure 9:
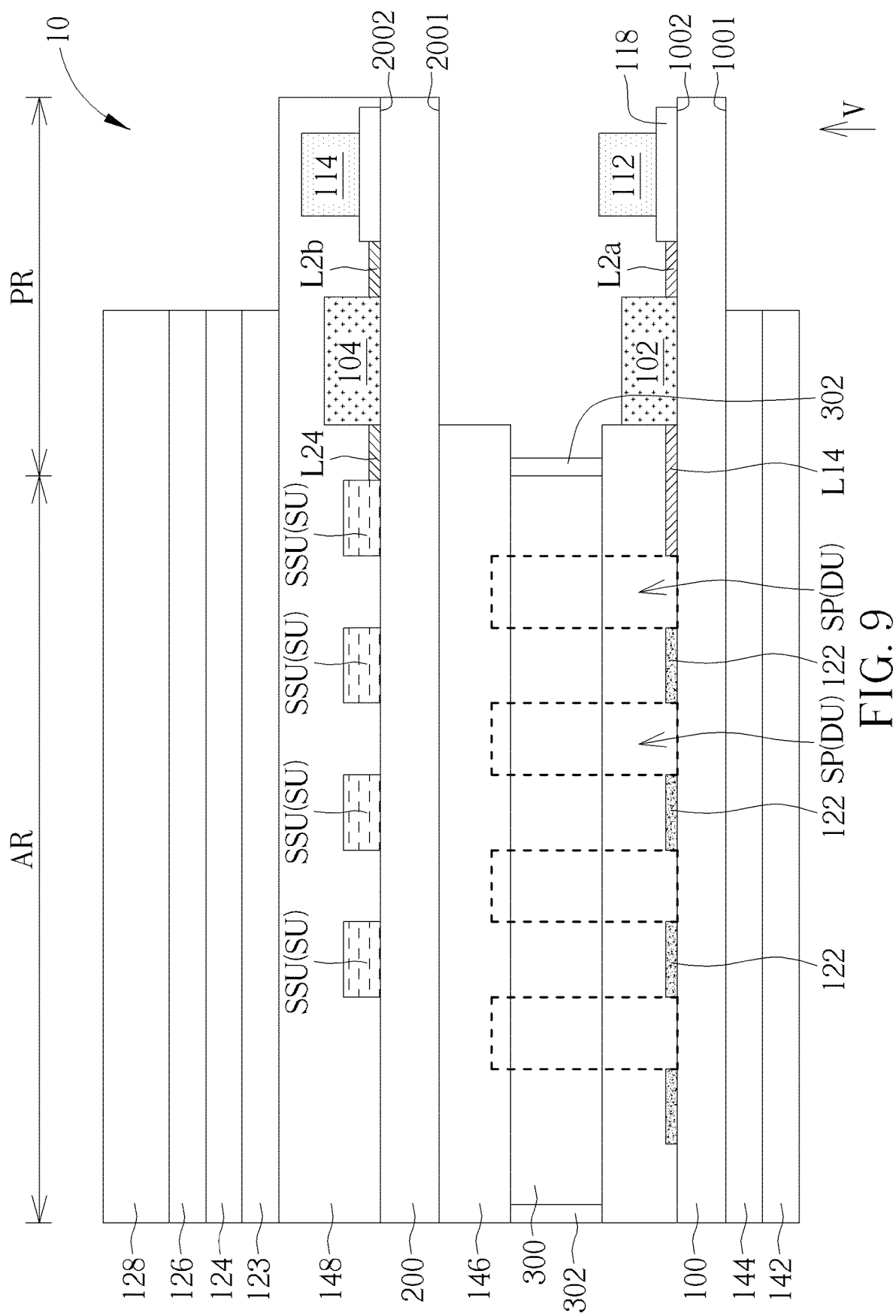
FIG. 9 is a schematic sectional view of an electronic device according to a sixth embodiment of the present disclosure.

Please refer to FIG. 9, which is a schematic sectional view of an electronic device according to a sixth embodiment of the present disclosure. The present embodiment is different from the fifth embodiment in that the sensor unit SU (such as the sub-sensor units SSU), the demux unit 104 and the integrated circuit chip 114 of the present embodiment may be disposed on the surface 2002 of the substrate 200, but the present disclosure is not limited thereto. Additionally, the sensing lines L24, the signal lines L2b or other signal lines (such as the sensing scan lines L22) may also be disposed on the surface 2002 of the substrate 200, but the present disclosure is not limited thereto.

Additionally, the electronic device 10 may selectively include a protective layer 148 disposed on the surface 2002 of the substrate 200 and at least cover the sensor unit SU, the demux unit 104, the integrated circuit chip 114, the sensing lines L24 or the signal lines L2b, but the present disclosure is not limited thereto. The protective layer 148 may include transparent insulating materials, and the insulating materials may include organic materials, inorganic materials, or a combination of aforementioned materials, but the present disclosure is not limited thereto. The adhesive layer 123, the polarizer 124, the adhesive layer 126 and the cover 128 may be disposed on the protective layer 148 in an order as described, but the present disclosure is not limited thereto. In some embodiments, the protective layer 148 may be omitted, and the adhesive layer 123 may be used to cover the sensor unit SU, the demux unit 104, the integrated circuit chip 114, the sensing lines L24 or the signal lines L2b, but the present disclosure is not limited thereto.

It is worth noting that, the abovementioned concept of reducing a quantity of signal lines electrically connected to the display unit DU or the sensor unit SU by the demux 106 (such as the demux unit 102 or the demux unit 104) in the peripheral region PR as mentioned in the first embodiment may also be applied in the present embodiment.

Figure 10:
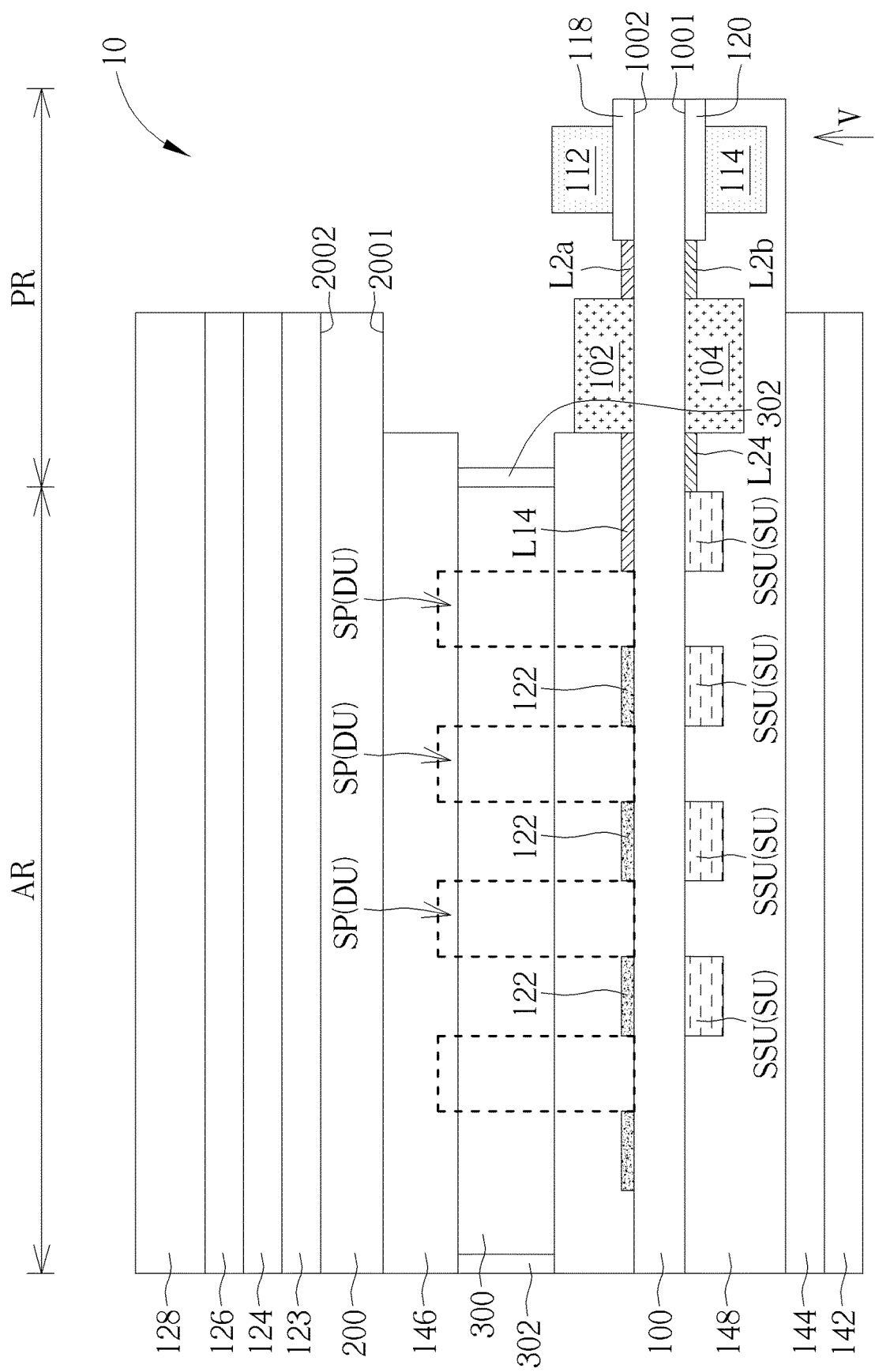
FIG. 10 is a schematic sectional view of an electronic device according to a seventh embodiment of the present disclosure.

Please refer to FIG. 10, which is a schematic sectional view of an electronic device according to a seventh embodiment of the present disclosure. The present disclosure is different from the fifth embodiment in that the sensor unit SU (such as the sub-sensor units SSU), the demux unit 104 and the integrated circuit chip 114 of the present embodiment may be disposed on the surface 1001 of the substrate 100, but the present disclosure is not limited thereto. Additionally, the sensing lines L24, the signal lines L2b and other signal lines (such as the sensing scan line L22) may also be disposed on the surface 1001 of the substrate 100, but the present disclosure is not limited thereto. In the present embodiment, the demux unit 102 may be disposed on the surface 1002 (which may also be called a first surface) of the substrate 100, the demux unit 104 may be disposed on the surface 1001 (which may also be called a second surface) of the substrate 100, and the surface 1001 may be located on a different side (or an opposite side) of the substrate 100 relative to the surface 1002.

Additionally, the electronic device 10 may selectively include a protective layer 148 disposed on the surface 1001 of the substrate 100 and at least cover the sensor unit SU, the demux unit 104, the integrated circuit chip 114, the sensing lines L24 or the signal lines L2b, but the present disclosure is not limited thereto. The adhesive layer 144 may be disposed between the polarizer 142 and the protective layer 148, but the present disclosure is not limited thereto. In some embodiments, the protective layer 148 may be omitted, and the adhesive layer 144 may be used to cover the sensor unit SU, the demux unit 104, the integrated circuit chip 114, the sensing lines L24 or the signal lines L2b, but the present disclosure is not limited thereto. In the present embodiment, the sensor unit SU may include ultrasonic sensors or other suitable types of sensors.

It is worth noting that, the abovementioned concept of reducing a quantity of signal lines electrically connected to the display unit DU or the sensor unit SU by the demux 106 (such as the demux unit 102 or the demux unit 104) in the peripheral region PR as mentioned in the first embodiment may also be applied in the present embodiment.

Figure 11:
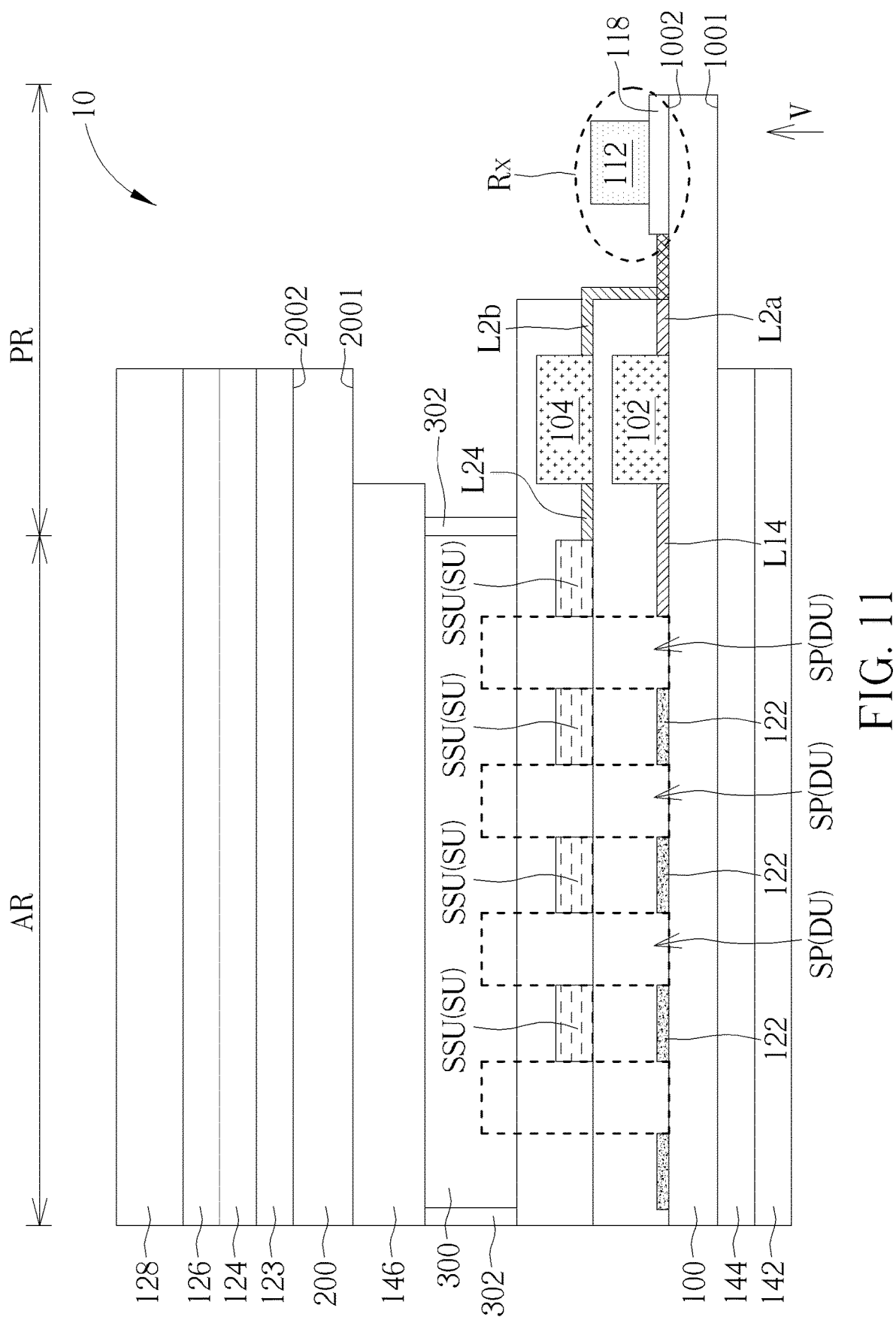
FIG. 11 is a schematic sectional view of an electronic device according to an eighth embodiment of the present disclosure.

Please refer to FIG. 11, which is a schematic sectional view of an electronic device according to an eighth embodiment of the present disclosure. The present disclosure is different from the fifth embodiment in that the demux unit 102 and the demux unit 104 of the present embodiment may be both disposed on the surface 1002 of the substrate 100. As an example, the sensor unit SU (such as the sub-sensor units SSU), the integrated circuit chip 114, the sensing lines L24, the signal lines L2b or other signal lines (such as the sensing scan lines L22) may also be disposed on the surface 1002 of the substrate 100, but the present disclosure is not limited thereto.

The sub-sensor units SSU, the sensing lines L24 or the sensing scan lines L22 (not shown in FIG. 11) may be disposed on the non-transparent elements 122 (such as the display scan lines L12, the data lines L14 etc.) or the thin film transistors TD of the sub-pixels SP, and the demux unit 104 may be disposed on the demux unit 102, but the present disclosure is not limited thereto. On the other hand, the signal line L2b of the present embodiment may have a folded portion. The folded portion may for example be the conductive line along an inclined surface or the conductive line inside the through hole, wherein a portion of the signal line L2b may be disposed on the signal line L2a, and another portion of the signal line L2b may be disposed on the same surface as the signal line L2a after being folded, but the present disclosure is not limited thereto. Additionally, the signal lines L2a and the signal lines L2b may all be electrically connected to the integrated circuit chip 112 through the conductive element 118; therefore, the electronic device 10 of the present embodiment may omit the integrated circuit chip 114, but the present disclosure is not limited thereto.

Figure 12:
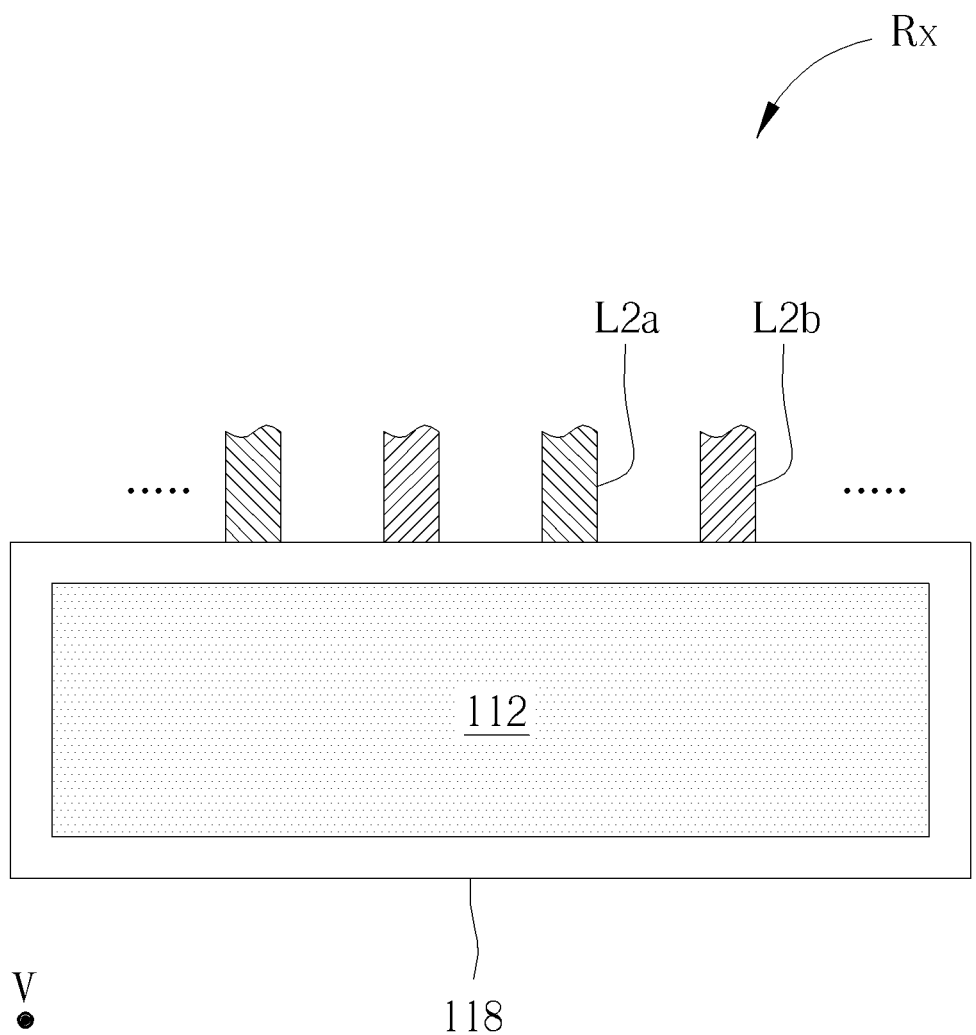
FIG. 12 is an enlarged schematic top view of a region Rx in FIG. 11.

Please refer to FIG. 12, which is an enlarged schematic top view of a region Rx in FIG. 11. In the region Rx, when the signal lines L2a and the signal lines L2b extend on the same surface, the signal lines L2a may be separate from the signal lines L2b such that the signal lines L2a and the signal lines L2b may be electrically insulated. For example, the signal lines L2a and the signal lines L2b may be alternately disposed (as shown in FIG. 12), or the signal lines L2a and the signal lines L2b may be separated by different regions, but the present disclosure is not limited thereto.

It is worth noting that, the abovementioned concept of reducing a quantity of signal lines electrically connected to the display unit DU or the sensor unit SU by the demux 106 (such as the demux unit 102 or the demux unit 104) in the peripheral region PR as mentioned in the first embodiment may also be applied in the present embodiment.

Figure 13:
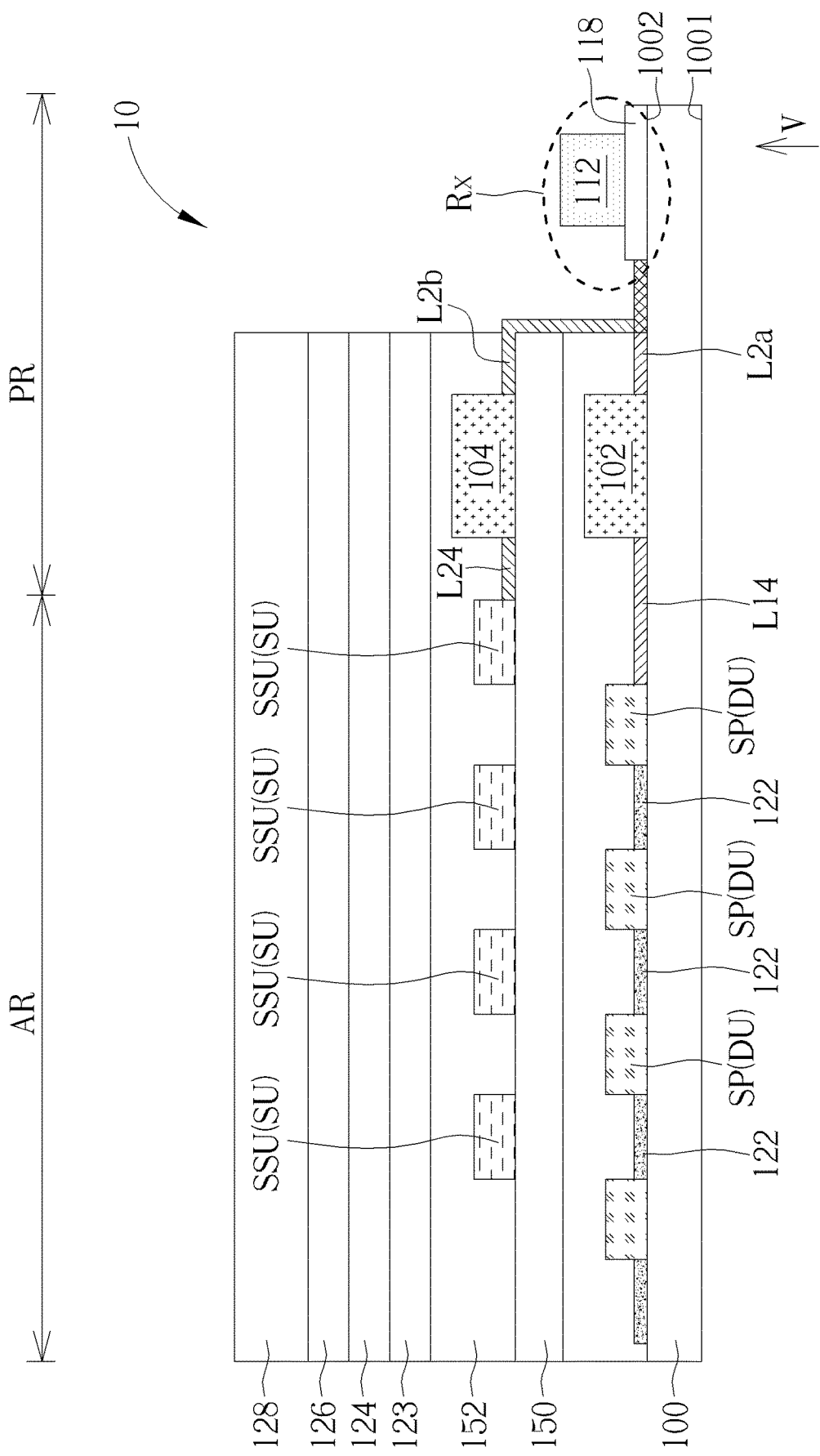
FIG. 13 is a schematic sectional view of an electronic device according to a ninth embodiment of the present disclosure.

Please refer to FIG. 13, which is a schematic sectional view of an electronic device according to a ninth embodiment of the present disclosure. The present embodiment is different from the eighth embodiment in that the sub-pixels SP of the display unit DU of the present embodiment may include self-emitting organic light-emitting diodes (OLEDs) or inorganic light-emitting diodes (LEDs), and thin film transistors that are electrically connected to the organic light-emitting diodes or inorganic light-emitting diodes. The electronic device of the present embodiment may choose not to be configured with a backlight module. The OLED or the inorganic LED may include at least an upper electrode, a lower electrode and an organic or inorganic light-emitting material between the upper and the lower electrode, while the lower electrode may be electrically connected to the thin film transistor. Each OLED or inorganic LED may be disposed inside an opening of a pixel defining layer (PDL). A region of the sub-pixel SP of the present embodiment may be defined by the opening of the PDL, but the present disclosure is not limited thereto. Additionally, the non-transparent elements 122 of the present embodiment may for example include the display scan lines L12, the data lines L14, common voltage lines, power lines or other non-transparent elements, but the present disclosure is not limited thereto.

Since the semiconductor material of the PIN-type diode utilized in the sub-sensor unit SSU may be non-transparent, the sub-sensor unit SSU should avoid overlapping with a region occupied by the sub-pixels SP having self-emitting diodes in the V direction, so as not to affect the luminous efficacy; the non-transparent element 122 may be disposed next to a side of the diode or disposed under the diode, so as not to affect the luminous efficacy. In some embodiments, if the semiconductor material of the PIN-type diode is transparent, the sub-sensor unit SSU and the sub-pixel SP may be overlapped. In some other embodiments, the sensor unit SU may be a capacitive sensor unit. In such scenarios, since the electrode of the sub-sensor unit SSU may be transparent (with high transmittance) and have minimal effect on the light passing through the sub-pixel SP, the sub-sensor unit SSU may selectively overlap, partially overlap, or not overlap at all with the sub-pixel SP.

Additionally, the electronic device 10 may include a protective layer 150 and an insulating layer 152 while omitting the substrate 200 of the eight embodiment. The protective layer 150 may be disposed between the display unit DU and the sensor unit SU, the insulating layer 152 may at least cover the sensor unit SU or the demux unit 104, but the present disclosure is not limited thereto. The adhesive layer 123, the polarizer 124, the adhesive layer 126 and the cover 128 may be disposed on the protective layer 148 in the order as described, but the present disclosure is not limited thereto. As an example, the protective layer 150 may include a composite layer of inorganic/organic/inorganic materials, and the insulating layer 152 may include insulating materials, but the present disclosure is not limited thereto. The polarizer 124 of the present embodiment may include circular polarizers to provide anti-reflection effects, and the electronic device 10 of the present embodiment may omit the polarizer 142 and the adhesive layer 144 of the eighth embodiment, but the present disclosure is not limited thereto. Furthermore, the signal lines L2a and the signal lines L2b in the region Rx may have the features as shown in FIG. 12; for the sake of brevity, please refer to descriptions in the eighth embodiment, and they are not redundantly described herein.

It is worth noting that, the abovementioned concept of reducing a quantity of signal lines electrically connected to the display unit DU or the sensor unit SU by the demux 106 (such as the demux unit 102 or the demux unit 104) in the peripheral region PR as mentioned in the first embodiment may also be applied in the present embodiment.

In summary, an electronic device of the present disclosure integrates the display unit and the sensor unit inside the active region, wherein the display unit and the sensor unit may both be electrically connected to N signal lines within a peripheral region through M signal lines, and M may be greater than N. Herein, a demux may be used to electrically connect the M signal lines to the N signal lines. In this manner, a quantity of the signal lines within the peripheral region may be reduced, and a production cost, time, or a space occupied by the signal lines within the peripheral region may also be lowered.

Even though embodiments and advantages of the present disclosure have been described as above, it should be understood that those skilled in the art may modify, substitute or amend features of the present disclosure depending on design requirements without departing from the essence and scope of the present disclosure, so long as the features do not interfere with each other and an essence of the disclosure is maintained. Any modification, equivalent substitutions and improvements encompassed by the essence of the present disclosure should be considered as being within the scope of the present disclosure.

What is claimed is:

1. An electronic device, comprising:
   a display unit;
   a sensor unit;
   M first signal lines;
   N second signal lines;
   a first substrate and a second substrate disposed opposite to the first substrate, wherein the display unit is disposed on the first substrate, and the sensor unit is disposed on the second substrate;
   a first demultiplexer unit and a second demultiplexer unit, wherein the first demultiplexer unit electrically connects the display unit, and the second demultiplexer unit electrically connects the sensor unit, and
   a first integrated circuit chip and a second integrated circuit chip, wherein the first integrated circuit chip is electrically connected to the first demultiplexer unit and the display unit, and the second integrated circuit chip is electrically connected to the second demultiplexer unit and the sensor unit,
   wherein the display unit and the sensor unit are both electrically connected to the N second signal lines through the M first signal lines, M and N are natural numbers, and M is greater than N,
   wherein the M first signal lines comprise M1 data lines and M2 sensing lines, the M1 data lines are electrically connected between the display unit and the first demultiplexer unit, the M2 sensing lines are electrically connected between the sensor unit and the second demultiplexer unit, and M1 and M2 are natural numbers,
   wherein the N second signal lines comprise N1 signal lines and N2 signal lines, the N1 signal lines are electrically connected between the first demultiplexer unit and the first integrated circuit chip, the N2 signal lines are electrically connected between the second demultiplexer unit and the second integrated circuit chip, and N1 and N2 are natural numbers,
   wherein the first demultiplexer unit, the first integrated circuit chip, the M1 data lines and the N1 signal lines are disposed on the first substrate, and the second demultiplexer unit, the second integrated circuit chip, the M2 sensing lines and the N2 signal lines are disposed on the second substrate,
   wherein the display unit comprises a plurality of sub-pixels and the sensor unit comprises a plurality of sub-sensor units, and one of the plurality of sub-sensor units is disposed between two adjacent ones of the plurality of sub-pixels in a top view of the electronic device, and
   wherein a gap is included between the two adjacent ones of the plurality of sub-pixels, and at least a portion of the one of the plurality of sub-sensor units is overlapped with the gap.

2. The electronic device according to claim 1, wherein M1 is greater than M2.

3. The electronic device according to claim 1, wherein an area of the sensor unit is less than an area of the display unit.

4. The electronic device according to claim 1, further comprising an active region, wherein the first demultiplexer unit and the second demultiplexer unit are disposed on a side of the active region.

5. The electronic device according to claim 1, further comprising an active region, wherein the first demultiplexer unit and the second demultiplexer unit are disposed on opposite sides of the active region.

* * * * *